(12) United States Patent
Kucklick

(10) Patent No.: US 8,025,648 B2
(45) Date of Patent: Sep. 27, 2011

(54) EXTRAVASATION MINIMIZATION DEVICE

(75) Inventor: Theodore R. Kucklick, Los Gatos, CA (US)

(73) Assignee: Cannuflow, Inc., San Jose, CA (US)

(*) Notice: Subject to any disclaimer, the term of this patent is extended or adjusted under 35 U.S.C. 154(b) by 1096 days.

(21) Appl. No.: 11/335,077

(22) Filed: Jan. 18, 2006

(65) Prior Publication Data
US 2007/0173754 A1     Jul. 26, 2007

(51) Int. Cl.
  *A61M 5/00*     (2006.01)
(52) U.S. Cl. ........................... 604/264; 604/541
(58) Field of Classification Search ............ 604/19, 604/21, 27, 500, 540, 319, 264, 272, 543, 604/506, 507, 508, 521, 541, 73, 524
See application file for complete search history.

(56) References Cited

U.S. PATENT DOCUMENTS

| | | | |
|---|---|---|---|
| 4,681,570 A * | 7/1987 | Dalton | 604/524 |
| 4,834,724 A | 5/1989 | Geiss et al. | |
| 4,881,939 A | 11/1989 | Newman | |
| 5,533,986 A * | 7/1996 | Mottola et al. | 604/264 |
| 5,620,428 A * | 4/1997 | Hand | 604/317 |
| 5,817,072 A | 10/1998 | Lampropoulos et al. | |
| 5,871,475 A * | 2/1999 | Frassica | 604/264 |
| 2003/0055373 A1 * | 3/2003 | Sramek et al. | 604/19 |
| 2005/0203342 A1 | 9/2005 | Kucklick et al. | |
| 2005/0215991 A1 | 9/2005 | Altman et al. | |

* cited by examiner

*Primary Examiner* — Christopher D Koharski
(74) *Attorney, Agent, or Firm* — Susan L. Crockett, Esq.; Crockett & Crockett, PC

(57) ABSTRACT

The devices and methods shown provide for the minimization of extravasation during arthroscopic surgery. The extravasation minimization device allows a surgeon to drain excess fluids from the soft tissue surrounding the surgical field during arthroscopic surgical procedures.

4 Claims, 5 Drawing Sheets

EXTRAVASATION MINIMIZATION DEVICE

FIELD OF THE INVENTIONS

The inventions described below relate to the field arthroscopic surgery and more specifically, to fluid management during arthroscopic shoulder surgery.

BACKGROUND OF THE INVENTIONS

During minimally invasive surgeries, surgical instruments such as trocars, cannulas, and optical medical devices, including endoscopes, cystoscopes, arthroscopes, laparoscopes, etc., are inserted through small incisions or portals in a patient's body or body cavity and manipulated to perform surgical procedures within the patient. Minimally invasive surgical procedures are safer than open surgery and result in quicker patient recovery, shorter hospital stays, and lower health care costs. Accordingly, minimizing invasiveness continues to be of importance, and there is a continuing need for devices and methods that achieve this objective.

One area that has benefited from minimally invasive surgical techniques is shoulder surgery. Shoulder surgery has evolved over the last several years from being an open surgical procedure to an arthroscopic surgical procedure. This evolution is the result of technological advances in equipment, instruments and implants.

During surgery, fluid is introduced into the surgical site to expand the joint and control bleeding. A major concern involving arthroscopic surgery of the shoulder is extravasation. Extravasation is the migration of interstitial fluid such as blood, irrigation fluids or medications into tissue surrounding an infusion site. Fluid escaping into the soft tissues of the shoulder and the periscapular region can have adverse effects on the patient. Some of these effects include tracheal compression, the accumulation of blood or clots in the joint (hemarthrosis), the forming of blood clots in veins (thrombophlebitis), arterial injury, nerve injury, the compression of blood vessels and nerves surrounding the joint (compartment syndrome), and infection. These effects cause longer recovery time as well as pain and discomfort in patients. Extravasation occurring during surgery can also cause premature collapse of the surgical field forcing surgeons to rush procedures. Because of the effects caused by extravasation, devices and methods are needed to reduce extravasation during arthroscopic shoulder surgery.

SUMMARY

The devices and methods shown below provide for the minimization of fluid extravasation during arthroscopic surgery. The extravasation minimization device allows a surgeon to drain fluids from the soft tissue surrounding the surgical field while using current arthroscopic surgical instruments. The extravasation minimization device comprises a hollow helical-shaped structure sized and dimensioned to be disposed about an outer surface of a cannula. Drainage holes in fluid communication with a drainage lumen are disposed on the outer surface of the helical structure. The proximal portion of the extravasation minimization device is provided with a fluid port, a manifold and other means of controlling the flow of fluid inside the extravasation minimization device. Each drainage hole communicates with one or more of the drainage lumens inside the structure, thereby allowing fluid to flow between the surgical field and sources or sinks located outside the patient. The extravasation minimization device allows the surgeon to reduce the amount of fluid extravasation occurring in surrounding tissue.

DETAILED DESCRIPTION OF THE INVENTIONS

Figure 1:
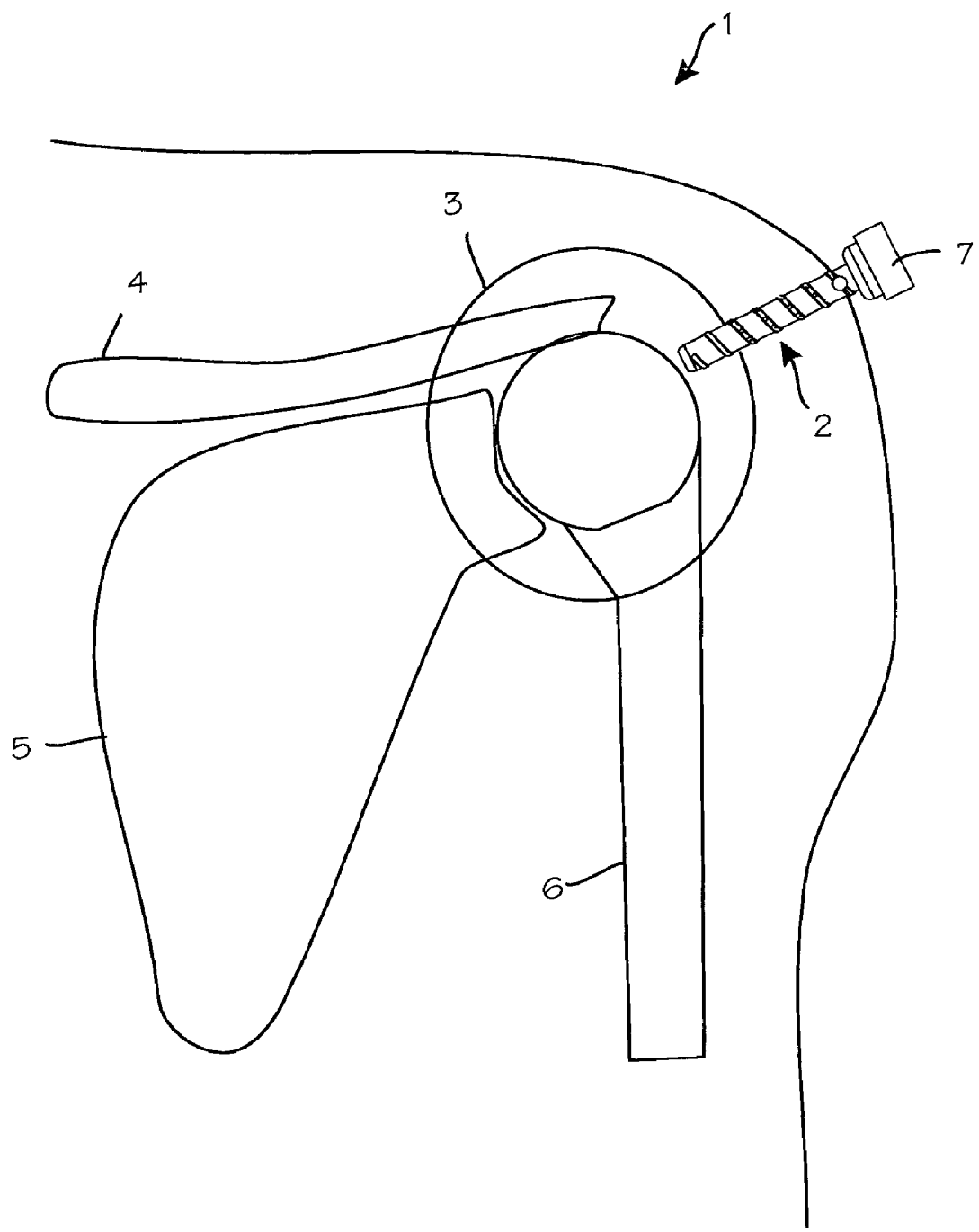
FIG. 1 illustrates a method of performing arthroscopic surgery on a patient using the extravasation minimization device.

FIG. 1 illustrates a method of performing arthroscopic surgery on a patient's shoulder 1 using the extravasation minimization device 2. The extravasation minimization device is shown inserted into the joint capsule 3 of a shoulder of a patient. Various anatomical landmarks are depicted including the patient's clavicle 4, scapula 5 and humerus 6. The extravasation minimization 2 device is disposed about an arthroscopic instrument 7 such as an arthroscope having a rigid cannula.

During arthroscopic shoulder surgery, the surgeon introduces the arthroscope into the shoulder via a first portal in order to visualize the surgical field. A trimming instrument is introduced through a second portal to remove or trim tissue that the surgeon determines should be removed or trimmed. Optionally, an irrigating instrument may be introduced through a third portal in order to distend the joint, and/or irrigate the surgical field to maintain a clear view. Other arthroscopic instruments used in arthroscopic surgery may include an endoscope, awl, pick or shaver.

Figure 2:
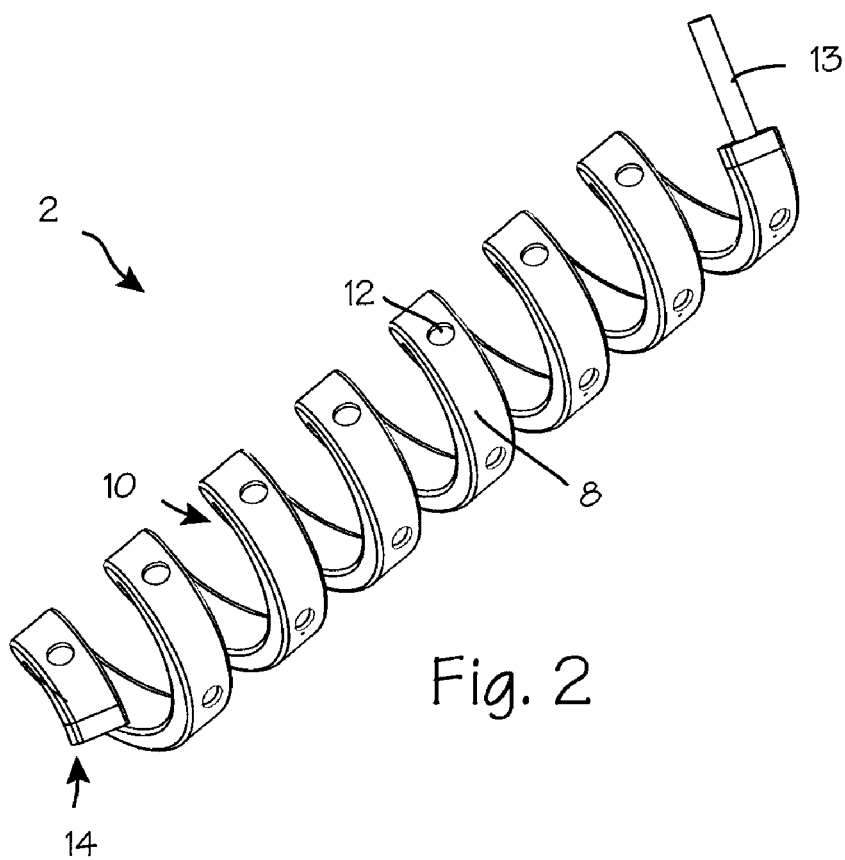
FIG. 2 is an isometric view of an extravasation minimization device.
Figure 3:
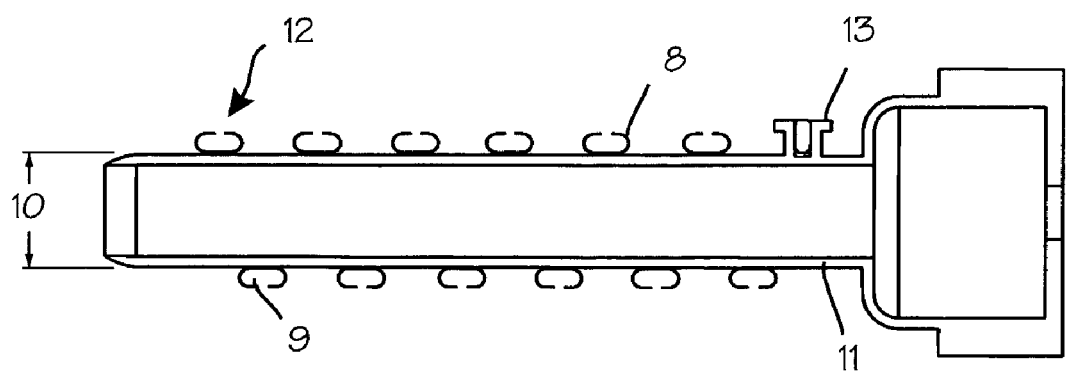
FIG. 3 is a longitudinal cross-sectional view of the extravasation minimization device disposed about a smooth surfaced working cannula.

FIG. 2 illustrates an isometric view of an extravasation minimization device 2 while FIG. 3 is a cross-sectional view of the extravasation minimization device 2 disposed over the outer diameter of a smooth surface cannula. The extravasation minimization device 2 comprises a helically wound flat tube or other helical structure 8 having one or more drainage lumens 9 extending therethrough. Wicking material may be disposed within the drainage lumens. The inner diameter 10 of the helical structure is sized and dimensioned to friction fit over the outer diameter 11 of a rigid cannula or arthroscopic instrument. The drainage lumen 9 is sized and dimensioned to accommodate fluid outflow from a surgical site. A plurality of drainage apertures 12 is disposed on the outer surface of the helical structure. The drainage apertures 12 are in fluid communication with the one or more drainage lumens disposed within the helical structure. The size of the drainage apertures 12 can be used to control the percolation rate of the device. The percolation rate of the device is the rate at which the device can drain interstitial fluid from surrounding tissue. The proximal portion of the extravasation minimization device is provided with a fluid port 13 or other adapter. The fluid port 13 or adapter provides for the removal of fluid from the drainage lumens through operable use of a vacuum source or sink of wicking material. The fluid port 13 is placed in fluid communication with the drainage lumens 9 and in fluid communication with a vacuum source. The fluid port 13 may be provided with or coupled to other means of controlling the flow of fluid and or the amount of suction inside the extravasation minimization device. The means for controlling suction and fluid flow may include valves, switches and computer based control systems. The distal tip 14 of the helical structure 8 is close-ended and may be arcuate in shape preventing damage to tissue in the surgical field. Each drainage aperture 12 is in fluid communication with one or more of the drainage lumens 9, thereby allowing fluid to flow between the surgical field and vacuum sources or sinks located outside the patient. Drainage apertures 12 in fluid communication with the drainage lumens 9 may also disposed along the inner diameter of the helical diameter of the extravasation minimization device.

The extravasation minimization device 2 may be manufactured from sterilizable biocompatible polymers such as nylon, polycarbonate urethane, polyurethane, polydimethylsiloxane and polyethylene glycol. The extravasation minimization device 2 can be part of a complete fluid management system comprising a fluid source, vacuum source, arthroscopic surgical pump and control system. An over pressure valve can be operably coupled to the extravasation minimization device 2 to allow a drainage lumen in the device to open and drain the joint if the joint is over-pressurized by an arthroscopic pump.

Figure 4:
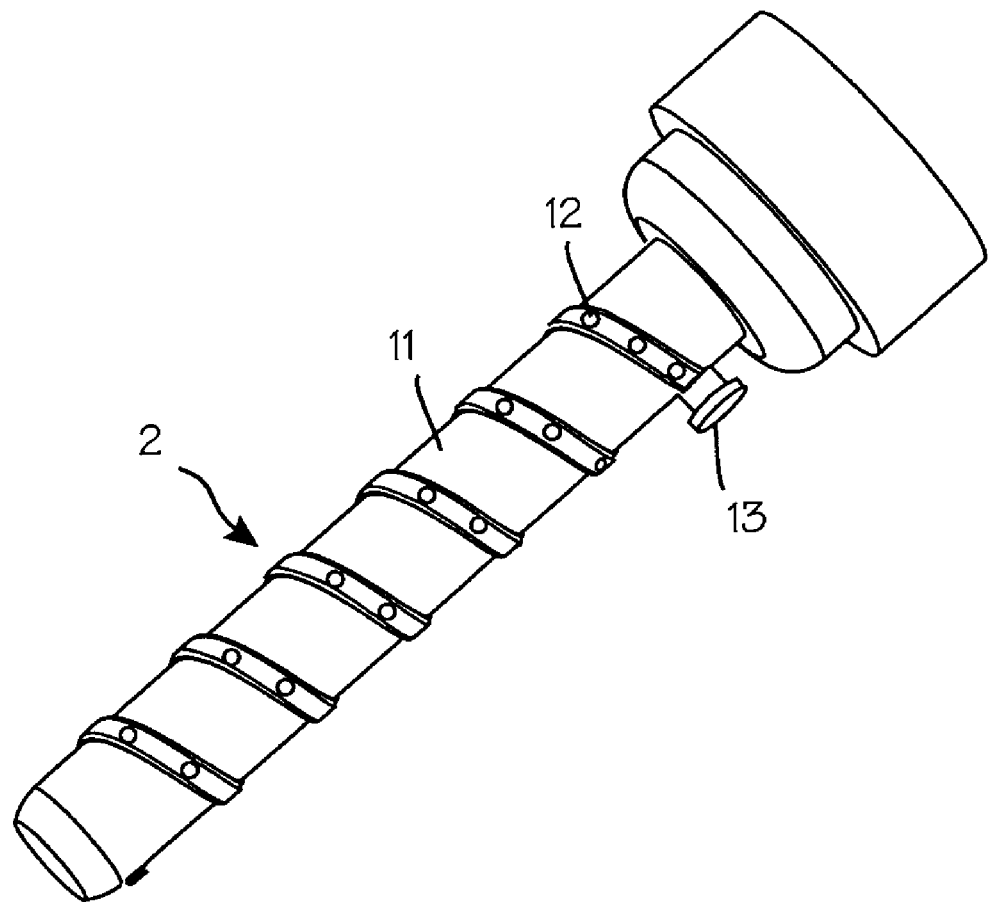
FIG. 4 is an isometric view of the extravasation minimization device disposed about the outer diameter of a smooth surfaced working cannula.

As depicted in the cross-sectional view in FIG. 3, the helical structure is a flat tube having a substantially rectangular cross-section and is provided with one or more drainage lumens. Drainage apertures are disposed on the outer surface of the helical structure. Drainage apertures may also be disposed on the side walls 15 of the helical structure between each helical turn as well as on the inner diameter 10 of helical structure. The inner diameter 10 is sized and dimensioned to accommodate the outer diameter of arthroscopic surgical instruments. As seen in FIG. 4, the extravasation minimization device 2 friction fits over the outer diameter 11 of the arthroscopic instrument or cannula when the helical structure is disposed about the arthroscopic instrument allowing the extravasation minimization device to be removeably coupled to the arthroscopic instrument.

Figure 5:
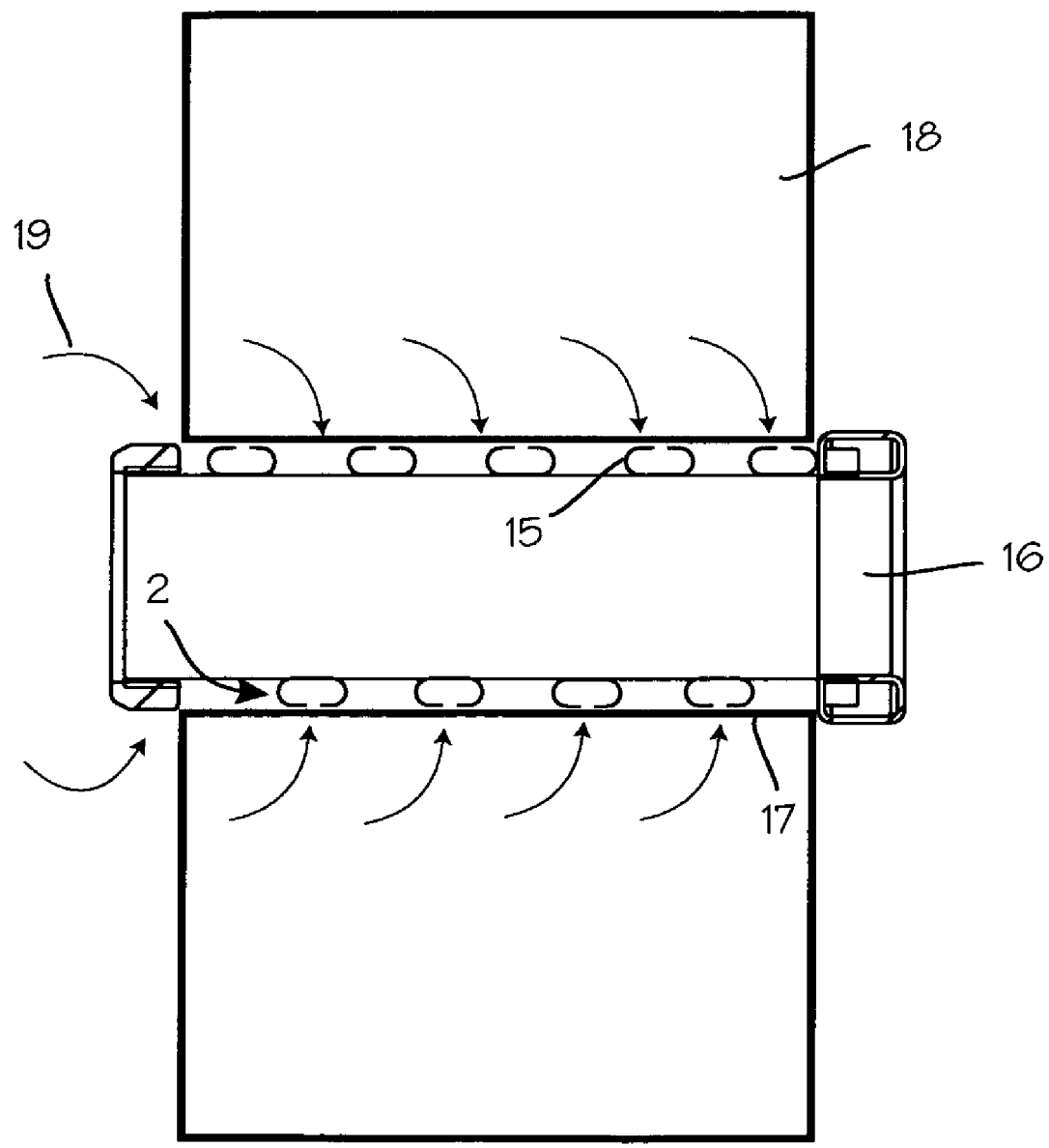
FIG. 5 is a longitudinal sectional view of the extravasation minimization device in shoulder tissue.

FIG. 5 shows a longitudinal sectional view of the extravasation minimization device 23 disposed over a working cannula 16 in shoulder tissue 18. The device is disposed within a surgical portal 17 created by a surgeon in a patient. The inner diameter of the helical structure allows the extravasation minimization device 2 to be disposed about an arthroscopic device such as a cannula 16. During arthroscopic surgical procedures, pressurized fluid is used to distend the joint, irrigate the surgical site and disrupt tissue bleeding. The pressurized fluid, blood and debris are drained from shoulder tissue 18 surrounding the surgical site through drainage apertures. The device 2 drains excess fluid 19 passing out of a surgical site into surrounding soft tissues in the shoulder. Removal of fluid, blood and debris reduces the amount of fluid left in the shoulder tissue thereby minimizing extravasation. In an effort to further minimize extravasation, the percolation rate of the extravasation minimization device is greater than the percolation rate of the surrounding tissue 18. The percolation rate of the surrounding tissue is the rate at which surrounding tissue absorbs fluid from the surgical field. The difference in percolation rates is preferably about 10% to about 15% in order to maintain pressure in the joint during surgery.

Figure 6:
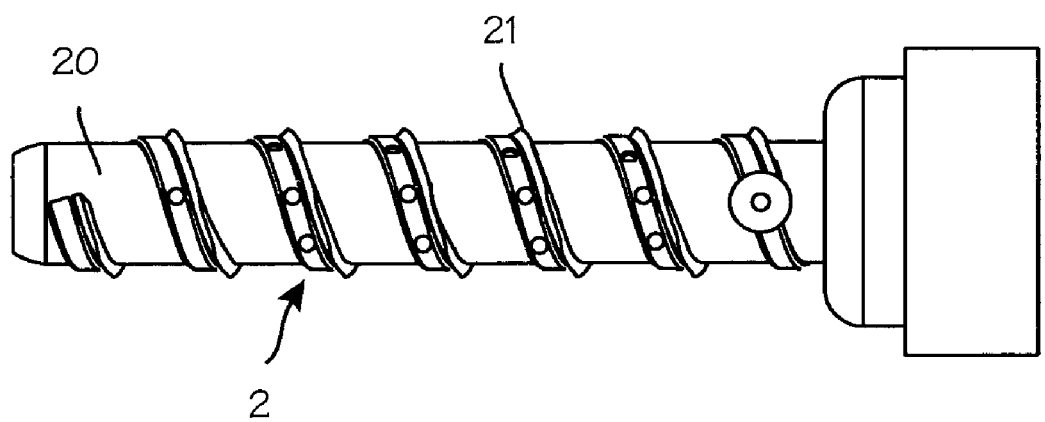
FIG. 6 is illustrates an extravasation minimization device disposed over a threaded cannula.

The extravasation minimization device 2 may also be used in conjunction with a screw threaded working cannula 20 as shown in FIG. 6. Here, the helical structure of the extravasation minimization device is disposed between the lead of the screw threads 21 on the outer surface of the cannula. Screw threads or other types of ridges disposed on the outer surface of the cannula prevent the cannula from being easily removed during surgery. This combination of a threaded cannula 20 and an extravasation minimization device provides for the benefit of anchoring the device while draining excess fluid.

While the preferred embodiments of the devices and methods have been described in reference to the environment in which they were developed, they are merely illustrative of the principles of the inventions. Other embodiments and configurations may be devised without departing from the spirit of the inventions and the scope of the appended claims.

I claim:

1. A system for performing arthroscopic surgery comprising:

an arthroscopic instrument;

an extravasation minimization device disposed about an outer diameter of the arthroscopic instrument, said extravasation minimization device comprising a helical structure having a drainage lumen disposed therein, said helical structure characterized by a distal end, a proximal end and an inner diameter sized and dimensioned to be removably disposed over the arthroscopic instrument, and a plurality of drainage apertures disposed on the outer surface of the helical structure in fluid communication with the drainage lumen; and a vacuum source in fluid communication with the drainage lumen;

wherein said helical structure is structured to allow fluid to flow through the drainage lumen, from a surgical site to a vacuum source, when said extravasation minimization device is disposed within an arthroscopic workspace; and wherein the arthroscopic instrument comprises a threaded surface working cannula wherein the helical structure is disposed between the lead of the screw threads.

2. A system for performing arthroscopic surgery comprising:

an arthroscopic instrument;

an extravasation minimization device disposed about an outer diameter of the arthroscopic instrument, said extravasation minimization device comprising a helical structure having a drainage lumen disposed therein, said helical structure characterized by a distal end, a proximal end and an inner diameter sized and dimensioned to be removably disposed over the arthroscopic instrument, and a plurality of drainage apertures disposed on the outer surface of the helical structure in fluid communication with the drainage lumen; and a vacuum source in fluid communication with the drainage lumen;

wherein said helical structure is structured to allow fluid to flow through the drainage lumen, from a surgical site to a vacuum source, when said extravasation minimization device is disposed within an arthroscopic workspace; and further comprising a threaded surface working cannula wherein the helical structure is disposed between the lead of the screw threads.

3. A system for performing arthroscopic surgery comprising:

an arthroscopic instrument;

an extravasation minimization device disposed about an outer diameter of the arthroscopic instrument, said extravasation minimization device comprising a helical structure having a drainage lumen disposed therein, said helical structure characterized by a distal end, a proximal end and an inner diameter sized and dimensioned to be removably disposed over the arthroscopic instrument, and a plurality of drainage apertures disposed on the outer surface of the helical structure in fluid communication with the drainage lumen; and a vacuum source in fluid communication with the drainage lumen;

wherein said helical structure is structured to allow fluid to flow through the drainage lumen, from a surgical site to a vacuum source, when said extravasation minimization device is disposed within an arthroscopic workspace; and wherein the arthroscopic instrument comprises a threaded surface working cannula wherein the helical structure complements the threaded surface working cannula.

4. A system for performing arthroscopic surgery comprising:

an arthroscopic instrument;

an extravasation minimization device disposed about an outer diameter of the arthroscopic instrument, said extravasation minimization device comprising a helical structure having a drainage lumen disposed therein, said helical structure characterized by a distal end, a proximal end and an inner diameter sized and dimensioned to be removably disposed over the arthroscopic instrument, and a plurality of drainage apertures disposed on the outer surface of the helical structure in fluid communication with the drainage lumen; and a vacuum source in fluid communication with the drainage lumen;

wherein said helical structure is structured to allow fluid to flow through the drainage lumen, from a surgical site to a vacuum source, when said extravasation minimization device is disposed within an arthroscopic workspace; and further comprising a threaded surface working cannula wherein the helical structure complements the threaded surface working cannula.

* * * * *